United States Patent [19]

Stahly

[11] Patent Number: 5,008,417

[45] Date of Patent: Apr. 16, 1991

[54] HALOALKYLATION PROCESS

[75] Inventor: G. Patrick Stahly, Baton Rouge, La.

[73] Assignee: Ethyl Corporation, Richmond, Va.

[21] Appl. No.: 525,827

[22] Filed: May 21, 1990

[51] Int. Cl.$^5$ ............................ C07F 7/22; C07F 7/30; C07F 9/02
[52] U.S. Cl. ...................................... 556/104; 556/81; 556/87; 568/8; 570/102
[58] Field of Search ...................... 556/13, 81, 87, 95, 556/104; 568/8; 570/102

[56] References Cited

U.S. PATENT DOCUMENTS

| | | | |
|---|---|---|---|
| 4,052,426 | 10/1977 | Wehner et al. | 556/104 X |
| 4,301,085 | 11/1981 | Wehner et al. | 556/104 |
| 4,322,363 | 3/1982 | Wagner | 556/104 |
| 4,374,778 | 2/1983 | Plum et al. | 556/104 X |
| 4,694,091 | 9/1987 | Kerherve et al. | 556/104 |

Primary Examiner—Arthur C. Prescott
Attorney, Agent, or Firm—Richard J. Hammond

[57] ABSTRACT

A process for the haloalkylation of certain tin, phosphorus and germanium halides is disclosed. The process is carried out typically in a halocarbon solvent at temperatures of less than 0° C. using as the haloalkylating reagent an admixture of a haloalkyl halide and tris(lower alkylamino)phosphine.

29 Claims, No Drawings

HALOALKYLATION PROCESS

FIELD OF THE INVENTION

This invention relates to a process for the haloalkylation of certain organometallic compounds.

BACKGROUND

Trifluoromethyl/metal compounds have found limited use in the prior art as intermediates for the preparation of certain biological or pharmaceutical reagents.

However, the prior art discloses that trifluoromethyl-substituted organometallic compounds, where the metal is electropositive, are difficult to form. According to the literature, because of the strong electronegative fluorine atoms, a positive charge is induced on the trifluoromethyl carbon atoms. Stability of any bond formed between an electropositive element and such carbon atom is adversely affected. As such, in the typical reaction to form these trifluoromethyl-substituted metal compounds, the compound resulting is principally derived from a difluoromethyl carbon elimination and rearrangement, the end result being to produce a metal fluoride. For example, for trifluoromethylboron compounds, the positive charge on boron may be removed either by coordination of a fourth ligand or by ($\pi$—$\pi$) bonds. As such, it is not surprising to find that the majority of known trifluoromethylboron compounds are derived from the tetravalent boron e.g. $CF_3BF_3^-$; $(CF_3)_2BF_2^-$; $CF_3BF_2 \cdot N(CH_3)_3$ and the like.

Recently, a process has been developed where trivalent boron compounds have been manufactured by using a phosphorus salt combined with the $CF_3$ containing halide e.g. $P[N(C_2H_5)]_3$ and a $CF_3$ bromide. The non-isolable intermediate $[(C_2H_5)_2N]_3PBr^+$ $CF_3^-$ is believed to be the active trifluoromethyl transfer agent for the reaction. See for example Bärger, et al, Journal of Fluorine Chemistry 31 89-92 (1989). While the desired product (trifluoromethyl amino borane) was identified, yields of product were severely depressed (25%).

The phosphorus route for producing trifluoromethyl-metal compounds has also been applied to the preparation of silicon compounds. See, Ruppert, et al Tetrahedron Letters 25 2195 (1984). For example, starting with trimethyl silicon chloride 90% yields of trifluoromethyl(trimethyl)silane are obtained. Similar success has been obtained by using aminosilanes where both bis and tris trifluoromethyl compounds have been isolated. See Chemical Abstracts Selects; Organofluorine Chemistry, 111 9, no. 115-298 f.

Accordingly, there is a need to more fully develop the chemistry of the haloalkylation process and prepare and study the ease of preparation and reactivity of the haloalkylated metal compounds.

SUMMARY OF THE INVENTION

Accordingly this invention provides a process developed for preparation of certain organo tin, phosphorus and germanium compounds. The starting compounds are represented by the following formula:

$$R_xSnZ_y, R_{x1}{}^1PZ_{y1}, \text{ and } R_{x2}{}^2GeZ_{y2}$$

wherein R, $R^1$ and $R^2$ are the same or different and are $C_1$ to $C_6$ linear or branched alkyl; phenyl unsubstituted or substituted with $C_1$ to $C_6$ linear or branched alkyl, or halo; amino unsubstituted or having at least one hydrogen substituted with $C_1$ to $C_6$ linear or branched alkyl or phenyl unsubstituted or substituted with $C_1$ to $C_6$ linear or branched alkyl; Z is halo; and x, y, $x_2$ and $y_2$ are integers from 1 to 3; and $x_1$ and $y_1$ are integers from 1 to 4, with the proviso that the sum of x and y and the sum of $x_2$ and $y_2$ is equal to 4 and the sum of $x_1$ and $y_1$ is at least 3 but not greater then 5 with a haloalkylating reagent comprising an admixture of a haloalkyl halide with a tris(di $C_1$ to $C_6$ linear or branched alkylamino)-phosphine and forming a compound selected from the group $$R_xSnZ'_y, R_{x1}{}^1PZ'_{y1}, \text{ and } R_{x2}{}^2GeZ'_{y2}$$

where R, $R^1$, $R^2$, x, $x_1$, $x_2$, y, $y_1$ and $y_2$ are as previously defined and $Z'$ is haloalkyl.

DESCRIPTION OF THE PREFERRED EMBODIMENTS

The inventors of the prevent invention have developed a novel process for the preparation of certain tin, phosphorus and germanium halo alkyl organic compounds that are intermediates useful in the preparation of agricultural and pharmaceutical compositions.

The process involves treating certain tin, phosphorus and germanium compounds with a haloalkylating reagent composition.

The compounds treated by the process of the present invention are selected from the group $$R_xSnZ_y, R_{x1}{}^1PZ_{y1}, \text{ and } R_{x2}{}^2GeZ_{y2}$$

where R, $R^1$ and $R^2$ are the same or different and are $C_1$ to $C_6$ linear or branched alkyl; phenyl unsubstituted or substituted with $C_1$ to $C_6$ linear or branched alkyl or halo; amino unsubstituted or having at least one hydrogen substituted with $C_1$ to $C_6$ linear or branched alkyl; Z is halo and x, y, $x_2$ and $y_2$ are integers from 1 to 3; and $x_1$ and $y_1$ are integers from 1 to 4 with the proviso that the sum of x and y and the sum of $x_2$ and $y_2$ is equal to 4 and the sum of $x_1$ and $y_1$ is at least 3 but not greater than 5.

In the treated compounds of the present invention, those preferred in the process of the present invention are those where R, $R^1$ and $R^2$ are the same or different and are methyl, ethyl, isopropyl, phenyl, 2-methylphenyl, 4-methylphenyl, 2-chlorophenyl, 4-chlorophenyl, amino, N-methylamino, N,N-dimethylamino, N-phenylamino and N,N-diphenylamino. Preferably, Z is chloro or bromo.

The most preferred compounds treated in accordance with the process of the present invention are those tin, phosphorus and germanium compounds of the formula:

$$R_3SnZ, R_2{}^1PZ \text{ or } R_3{}^2GeZ$$

where R, $R^1$ and $R^2$ are the same or different and are $C_1$ to $C_6$ linear or branched alkyl; phenyl unsubstituted or substituted with $C_1$ to $C_6$ linear or branched alkyl or halo; amino unsubstituted or having at least one hydrogen substituted with $C_1$ to $C_6$ linear or branched alkyl; Z is halo and x, y, $x_2$ and $y_2$ are integers from 1 to 3; and $x_1$ and $y_1$ are integers from 1 to 4 with the proviso that the sum of x and y and the sum of $x_2$ and $y_2$ is equal to 4 and the sum of $x_1$ and $y_1$ is at least 3 but not greater than 5.

Of the above most preferred compounds treated in accordance with the present invention particularly preferred are those compounds where R, $R^1$ and $R^2$ are the same or different and are methyl, ethyl, isopropyl, phenyl, 2-methylphenyl, 4-methylphenyl, 2-chlorophenyl, 4-chlorophenyl, amino, N-methylamino, N,N-dimethylamino, N-phenylamino or N,N-diphenylamino. Preferably, Z is chloro or bromo.

Tin compounds for use to be treated in accordance with the present invention include:
trimethyl tin chloride;
triethyl tin chloride;
tri-isopropyl tin bromide;
tri-n-butyl tin bromide;
phenyl-dimethyl tin chloride;
methyl-diphenyl tin chloride;
triphenyl tin chloride;
tri(4-methylphenyl) tin chloride;
tri(4-chlorophenyl) tin chloride;
triamino tin chloride;
tri(N-methylamino) tin chloride;
tri(N,N-dimethylamino) tin chloride;
tri(N-phenylamino) tin chloride; and
(N,N-diphenylamino) tin chloride.

Phosphorus compounds of use in the process of this present invention include:
dimethyl chlorophosphine;
diethyl bromophosphine;
di-isopropyl chlorophosphine;
di-n-butyl chlorophosphine;
methylphenyl chlorophosphine;
phenylmethyl chlorophosphine;
diphenyl chlorophosphine;
bis(4-methylphenyl)chlorophosphine;
bis(4-chlorophenyl)chlorophosphine;
diamino chlorophosphine;
bis(N-methylamino)chlorophosphine;
bis(N,N-dimethylamino)chlorophosphine;
bis(N-phenylamino)chlorophosphine; and
bis(N,N-diphenylamino)chlorophosphine.

Germanium compounds of use in the process of the present invention include:
trimethyl germanium chloride;
triethyl germanium chloride;
tri-isopropyl germanium bromide;
tri-n-butyl germanium bromide;
phenyl-dimethyl germanium chloride;
methyl-diphenyl germanium chloride;
triphenyl germanium chloride;
tri(4-methylphenyl) germanium chloride;
tri(4-chlorophenyl) germanium chloride;
triamino germanium chloride;
tri(N-methylamino) germanium chloride;
tri(N,N-dimethylamino) germanium chloride;
tri(N-phenylamino) germanium chloride; and
tri(N,N-diphenylamino) germanium chloride.

The tin, phosphorus and germanium compounds set forth herein are treated with a haloalkylating reagent by the process of the present invention. Such haloalkylating reagent comprises an admixture of a haloalkyl halide with a tris(di $C_1$ to $C_6$ linear or branched alkylamino)phosphine. The term "haloakyl" is intended to include those fluoro or chloro substituted alkyl groups ($C_1$ to $C_6$ linear or branched alkyl) such as illustrated by trichloromethyl, trifluoromethyl, difluorochloromethyl, dichlorofluoromethyl, 2,2,2-trifluoroethyl, 2,2,2-trichloroethyl, 2,2-difluoroethyl, 2,2-dichloroethyl and the like. The term "halide" includes iodo, bromo, and chloro.

The above haloalkyl halide, admixed with a tris (di $C_1$ to $C_6$ linear or branched alkylamino)phosphine typically in a halocarbon solvent form the haloalkylating reagents of the present invention. Preferably, the phosphorous compounds of use
in this reagent are the tris(di $C_1$ to $C_3$ linear or branched alkylamino) compounds and include tris(dimethylamino)phosphine; tris(diethylamino)phosphine, bis(diethylamino)monomethylaminophosphine, bis(dimethylamino)monoethylaminophosphine and the like.

Treatment of the above-disclosed tin, phorphorus and germanium compounds with the haloalkylating reagent produce compounds of the formula:

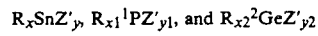

where R, $R^1$, $R^2$, x, $x_1$, $x_2$, y, $y_1$, $y_2$ are as defined previously and Z' is a haloalkyl group.

In the above compounds produced by the process of the present invention the preferred compounds produced include those where R, $R^1$ and $R^2$ are the same or different and are methyl, ethyl, isopropyl, phenyl, 2-methylphenyl, 4-methylphenyl, 2-chlorophenyl, 4-chlorophenyl, amino, N-methylamino, N,N-dimethylamino, N-phenylamino or N,N-diphenylamino. Preferably $Z^1$ is fluoroalkyl or chloroalkyl.

The most preferred compounds produced in accordance with the process of the present invention have the formula:

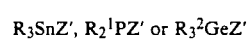

where R, $R^1$ and $R^2$ are the same or different and are $C_1$ to $C_6$ linear or branched alkyl; phenyl unsubstituted or substituted with $C_1$ to $C_6$ linear or branched alkyl, or halo; amino unsubstituted or having at least one hydrogen substituted with $C_1$ to $C_6$ linear or branched alkyl or phenyl unsubstituted or substituted with $C_1$ to $C_6$ linear or branched alkyl; and Z' is fluoroalkyl or chloroalkyl.

In the above most preferred compounds, those particularly preferred are where R, $R^1$ and $R^2$ are the same or different and are methyl, ethyl, isopropyl, phenyl, 2-methylphenyl, 4-methylphenyl, 2-chlorophenyl, 4-chlorophenyl, amino, N-methylamino, N,N-dimethylamino, N-phenylamino or N,N-diphenylamino.

As stated earlier, the above-mentioned compounds are treated with a haloalkylating reagent, typically in solution using a halocarbon solvent. The treatment is effective if carried out at relatively low temperatures, for example at about $-90°$ C. to about $0°$ C. While all of the haloalkylating reagent can be added at one time, it is preferred that the tris (di $C_1$ to $C_6$ linear or branched alkylamino)phosphine is added to a mixture of haloalkyl halide and metallorganic halide slowly most preferably over a period of about 15 minutes to about 60 minutes. Separation of the product produced by the process of the present invention is readily accomplished by ordinary separation techniques i.e., distillation, solvent extraction and the like.

The following Examples are for purposes of illustration only and are not intended to limit the process of this invention in any way.

EXAMPLES

Diphenyltrifluoromethvlphosohine

A flask equipped with a dry ice condenser was flame dried under a nitrogen stream, and charged with 3.1 mL (17 mmol) of chlorodiphenylphosphine and 10 mL of dichloromethane. After cooling the resulting solution to −78° C. and charging the condenser with dry ice and acetone, 4 mL (43 mmol) of bromotrifluoromethane (Freon 13B1) that had been condensed into a graduated tube was warmed to room temperature and allowed to distill into the flask. The cold solution was treated dropwise with 7 mL (26 mmol) of hexaethylphosphorous triamide, allowed to stir at "78° C. for 1 hour, and allowed to stir at room temperature overnight. Dilution with 50 mL of dichloromethane, water washing (three 50 mL portions), drying (MgSO$_4$), and concentration afforded a brown liquid which was purified by flash chromatography on 50g of silica gel (230–400 mesh) eluted with petroleum ether to give 2.9g (68% yield) of diphenyltrifluoromethylphosphine as a colorless liquid. $^{19}$F NMR (CDCl$_3$, relative to CFCl$_3$) −55.60 ppm (d, $J_{PF}$=73 Hz); $^{31}$P NMR (CDCl$_3$, relative to H$_3$PO$_4$) 3.11 ppm (quartet of pentets, $J_{PF}$=73 Hz, $J_{PH}$=8 Hz); mass spectrum (70 eV) m/z (relative intensity) 254 (41, M$^+$), 185 (74), 183 (100), 127 (23), 107 (40), 77 (26), 69 (65), 51 (54).

Diphenyltrifluoromethylphosphine Oxide

A solution of 1.0g (3.9 mmol) of diphenyltrifluoromethylphosphine (4) in 5 mL of acetone was treated with 0.5 mL (4.9 mmol) of 30% hydrogen peroxide. Within a few minutes an exothermic reaction occurred which caused the solution to reflux. After this had subsided, the solution was allowed to stand for 4 hours at room temperature and poured into 15 mL of water. The resulting aqueous mixture was extracted with three 10 mL portions of cichloromethane. The organic layers were combined, dried (MgSO$_4$), and concentrated to give 0.85g (80% yield) of diphenyltrifluoromethylphosphine oxide as a colorless liquid: $^{19}$F NMR (CDCl$_3$ relative to CF$_3$CO$_2$H) 5.86 ppm (d, $J_{PF}$=89 Hz); mass spectrum (70 eV) m/z (relative intensity) 201 (100, M-CF$_3$), 77 (23), 51 (16).

Tri-n-butyltrifluoromethyltin

A flask equipped with a dry ice condenser was flame dried under a nitrogen stream, then charged with 6.0 mL (22 mmol) of tri-n-butyltin chloride and 10 mL of dichloromethane. After cooling the resulting solution to −78° C. and charging the condenser with dry ice and acetone, 6.2 mL (66 mmol) of bromotrifluoromethane (Freon 13B1) that had been condensed into a graduated tube was warmed to room temperature and allowed to distill into the flask. The cooling bath was removed and the mixture was allowed to warm to the temperature of the refluxing Freon (−59° C.). To this cold solution was added, dropwise, 5.0 mL (28 mmol) of hexaethylphosphorous triamide. The resulting solution was stirred at reflux for 1 hour. Removal of the condenser and continued stirring for 2 hours resulted in evaporation of excess Freon and warming of the solution to room temperature. Water washing (three 10 mL portions) and distillation at 3 torr gave 2.9g of material of bp 95–104° C. GC analysis showed this contained 91% tri-n-butyltrifluoromethyltin: mass spectrum (70 eV) m/z (relative intensity) 287–291, 249–253, 231–236, 173–179, 135–139, and 117–121 (Sn-containing clusters, varying intensities), 57 (67), 41 (100).

2,2′-Ethylidenebis (4,6-di-tert-butylphenyl) trifluoromethylphosphonite

A flask equipped with a dry ice condenser was flame dried under a nitrogen stream, and charged with 12g (24 mmol) of 2,2′-ethylidenebis(4,6-di-tert-butylphenyl) chlorophosphite and 80 mL of dichloromethane. After cooling the resulting mixture to −78° C. and charging the condenser with dry ice and acetone, 6.8 mL of bromotrifluoromethane (Freon 13B1) that had been condensed into a graduated tube was warmed to room temperature and allowed to distill into the flask. The cold bath was replaced by an insulating bath and the mixture was allowed to reach the temperature of the refluxing freon (−59° C.). Then 9.3 mL (34 mmol) of hexaethylphosphorous triamide was added dropwise. The mixture was stirred cold for 1 hour and the condenser was removed to allow excess freon to distill away. The mixture was recooled to 0°–5° C. and filtered at the temperature. The filter cake was washed with 30 mL of ice-cold dichloromethane, triturated in 100 mL of refluxing dichloromethane, and filtered. Reduction in volume (to about 50 mL) and cooling of the mother liquor afforded 3.3g of white, crystalline solid. Gas chromatographic analysis of this indicated it was 96% 2,2′-ethylidenebis (4,6-di-tertbutylphenyl)trifluoromethylphosphonite and 4% compound 2,2′-ethylidenebis(4,6-di-tert-butylphenyl)chlorophosphonite (about 24% yield).

Material of sufficient purity for antioxidant testing was obtained as follows. A mixture of 4.0g of material obtained as described above and 0.5 mL of water in 25 mL of toluene was heated to reflux for 5 hours. While still hot the toluene was decanted from the water and then gravity filtered. Reduction in volume (to about 20 mL) and cooling of the filtrate afforded 2.8g of white, crystalline 2,2′-ethylidenebis (4,6-di-tert-butylphenyl)-trifluoromethylphosphonite (99.1% pure by GC): mp 267°–270° C.; $^1$H NMR (CDCl$_3$) 1.30 (s, 18H), 1.39 (s, 18H), 1.60 (d, 3H), 4.83 (q, 1H), 7.23 (m, 2H), 7.41 (m, 2H); $^{19}$F NMR (CDCl$_3$/C$_6$D$_6$, relative to CFCl$_3$)) 22.0 ppm (d, $J_{PF}$=73 Hz); $^{31}$P NMR (CDCl$_3$/C$_6$D$_6$, relative to H$_3$PO$_4$) 143.7 ppm (q, $J_{PF}$=73 Hz).

I claim:

1. A process for preparing haloalkyl-substituted compounds said process comprising treating a compound selected from the group

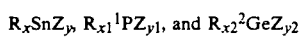

wherein R, R$^1$ and R$^2$ are the same or different and are C$_1$ to C$_6$ linear or branched alkyl, phenyl unsubstituted or substituted with C$_1$ to C$_6$ linear or branched alkyl or halo; amino unsubstituted or having at least one hydrogen substituted with C$_1$ to C$_6$ linear or branched alkyl or phenyl unsubstituted or substituted with C$_1$ to C$_6$ linear or branched alkyl; Z is halo; and x, y, x$_2$ and y$_2$ are integers from 1 to 3; and x$_1$ and y$_1$ are integers from 1 to 4, with the proviso that the sum of x and y and the sum of x$_2$ and y$_2$ is equal to 4 and the sum of x$_1$ and y$_1$ is at least 3 but not greater than 5 with a haloalkylating reagent comprising an admixture of a haloalkyl halide with a tris(di C$_1$ to C$_6$ linear or branched alkylamino)-phosphine and forming a compound selected from the group

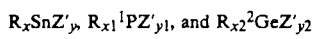

Z′ is a haloalkyl group and where R, R$^1$, R$^2$, x, x$_1$, x$_2$, y, y$_1$ and y$_2$ are as previously defined.

2. The process according to claim 1 wherein R, R$^1$ and R$^2$ are the same or different and are methyl, ethyl, 1-propyl, phenyl, 2-methylphenyl, 4-methylphenyl, 2- chlorophenyl, 4-chlorophenyl, amino, N-methylamino, N,N-dimethylamino, N-phenylamino, N,N-diphenylamino and Z is chloro or bromo.

3. The process of claim 2 wherein said haloalkylating reagent comprises an admixture of trifluoromethyl chloride or trifluoromethyl bromide with a tris(di $C_1$ to $C_6$ linear or branched alkylamino)phosphine.

4. The process of claim 3 wherein said tris(di $C_1$ to $C_6$ linear or branched alkylamino)phosphine is tris(diethylamino)phosphine.

5. The process of claim 1 wherein said treating is carried out at a temperature from about "100° C. to about 0° C.

6. A process for preparing a tris haloalkyl-substituted compound said process comprising treating $R_xSnZ_y$ wherein R is $C_1$ to $C_6$ or branched alkyl, phenyl unsubstituted or substituted with $C_1$ to $C_6$ linear or branched alkyl or halo, amino unsubstituted or having at least one hydrogen substituted with $C_1$ to $C_6$ linear or branched alkyl, or phenyl unsubstituted or substituted with $C_1$ to $C_6$ linear or branched alkyl, Z is halo and x and y are integers from 1 to 4 with the proviso that the sum of x and y is equal to 4 with a haloalkylating reagent comprising an admixture of a haloalkyl halide with a tris(di $C_1$ to $C_6$ linear or branched alkylamino)phosphine and forming $R_xSnZ'_y$ where R, x and y are as previously defined and Z' is haloalkyl.

7. The process of claim 6 wherein R is $C_1$ to $C_3$ linear or branched alkyl; phenyl unsubstituted or substituted with $C_1$ to $C_3$ linear or branched alkyl or halo; amino unsubstituted or having at least one hydrogen substituted with $C_1$ to $C_3$ linear or branched alkyl or phenyl unsubstituted or substituted with $C_1$ to $C_3$ linear or branched alkyl and x is greater than 1.

8. The process of claim 7 wherein R is methyl, ethyl, 1-propyl, phenyl, 2-methylphenyl, 4-methylphenyl, 2-chlorophenyl, 4-chlorophenyl, amino, N-methylamino, N,N-dimethylamino, N-phenylamino, N,N-diphenylamino and Z is chloro or bromo.

9. The process of claim 8 wherein said haloalkylating reagent comprises an admixture of trifluoromethyl chloride or trifluoromethyl bromide with tris(di$C_1$ to $C_3$ linear or branched alkylamino)phosphine.

10. The process of claim 9 wherein said tris(di$C_1$ to $C_3$ linear or branched alkylamino)phosphine is tris(diethylamino)phosphine.

11. The process of claim 10 wherein each R is the same.

12. The process of claim 10 wherein at least one R is different.

13. The process of claim 11 or 12 wherein said treating is carried out at a temperature from about $-100°$ C. to about 0° C.

14. A process for preparing a germanium trifluoromethyl-substituted compound said process comprising treating $R_{x2}{}^2GeZ_{y2}$ where $R^2$ is $C_1$ to $C_6$ linear or branched alkyl, phenyl unsubstituted or substituted with $C_1$ to $C_6$ linear or branched alkyl or halo, amino unsubstituted or having at least one hydrogen substituted with $C_1$ to $C_6$ linear or branched alkyl, or phenyl unsubstituted or substituted with $C_1$ to $C_6$ linear or branched alkyl, Z is halo and x and y are integers from 1 to 4 with the proviso that the sum of x and y is equal to 4 with a haloalkylating reagent comprising an admixture of a haloalkyl halide with a tris(di $C_1$ to $C_6$ linear or branched alkylamino)phosphine and forming $R_{x2}{}^2GeZ'_{y2}$ where $R^2$, $x_2$ and $y_2$ are as previously defined and Z' is haloalkyl.

15. The process of claim 14 wherein $R^2$ is $C_1$ to $C_3$ linear or branched alkyl; phenyl unsubstituted or substituted with $C_1$ to $C_3$ linear or branched alkyl or halo; amino unsubstituted or having at least one hydrogen substituted with $C_1$ to $C_3$ linear or branched alkyl or phenyl unsubstituted or substituted with $C_1$ to $C_3$ linear or branched alkyl and $x_2$ is greater than 1.

16. The process of claim 15 wherein $R^2$ is methyl, ethyl, 1-propyl, phenyl, 2-methylphenyl, 4-methylphenyl, 2-chlorophenyl, 4-chlorophenyl, amino, N-methylamino, N,N-dimethylamino, N-phenylamino, N,N-diphenylamino and Z is chloro or bromo.

17. The process of claim 16 wherein said haloalkylating reagent comprises an admixture of trifluoromethyl chloride or trifluoromethyl bromide with tris(di $C_1$ to $C_3$ linear or branched alkylamino)phosphine.

18. The process of claim 17 wherein said tris(di $C_1$ to $C_3$ linear or branched alkylamino)phosphine is tris(diethylamino)phosphine.

19. The process of claim 18 wherein each $R^2$ is the same.

20. The process of claim 18 wherein at least one $R^2$ is different.

21. The process of claim 19 or 20 wherein said treating is carried out at a temperature from about $-100°$ C. to about 0° C.

22. A process for preparing a phosphorus trifluoromethyl-substituted compound said process comprising treating $R_{x1}{}^1PZ_{y1}$ wherein $R^1$ is $C_1$ to $C_6$ linear or branched alkyl, phenyl unsubstituted or substituted with $C_1$ to $C_6$ linear or branched alkyl or halo, amino unsubstituted or having at least one hydrogen substituted with $C_1$ to $C_6$ linear or branched alkyl, or phenyl unsubstituted or substituted with $C_1$ to $C_6$ linear or branched alkyl, Z is halo and $x_1$ and $y_1$ are integers from 1 to 5 with the proviso that the sum of $x_1$ and $y_1$ equals at least 3 but not more than 5 with a haloalkylating reagent comprising an admixture of a haloalkyl halide with a tris(di $C_1$ to $C_6$ linear or branched alkylamino)phosphine and forming $R_{x1}PZ'_{y1}$ where $R_1$, $x_1$ and $y_1$ are as previously defined and Z' is haloalkyl.

23. The process of claim 22 wherein $R^1$ is $C_1$ to $C_3$ or branched alkyl; phenyl unsubstituted or substituted with $C_1$ to $C_3$ linear or branched alkyl or halo; amino unsubstituted or having at least one hydrogen substituted with $C_1$ to $C_3$ linear or branched alkyl or phenyl unsubstituted or substituted with $C_1$ to $C_3$ linear or branched alkyl and $x_1$ is greater than 1.

24. The process of claim 23 wherein $R^1$ is methyl, ethyl, 1-propyl, phenyl, 2-methylphenyl, 4-methylphenyl, 2-chlorophenyl, 4-chlorophenyl, amino, N-methylamino, N,N-dimethylamino, N-phenylamino, N,N-diphenylamino and Z is chloro or bromo.

25. The process of claim 24 wherein said haloalkylating reagent comprises an admixture of trifluoromethyl chloride or trifluoromethyl bromide with tris(di$C_1$ to $C_3$ linear or branched alkylamino)phosphine.

26. The process of claim 25 wherein said tris(di$C_1$ to $C_3$ linear or branched alkylamino)phosphine is tris(diethylamino)phosphine.

27. The process of claim 26 wherein each $R^1$ is the same.

28. The process of claim 26 wherein at least one $R^1$ is different.

29. The process of claim 27 or 28 wherein said treating is carried out at a temperature from about $-100°$ C. to about 0° C.

* * * * *